United States Patent
Jordfald et al.

(10) Patent No.: US 6,478,743 B2
(45) Date of Patent: Nov. 12, 2002

(54) TRANSESOPHAGEAL ULTRASOUND PROBE WITH IMAGING ELEMENT POSITION SENSOR IN SCANHEAD

(75) Inventors: Dag Jordfald, Horten (NO); Jiayu Chen, Palo Alto, CA (US); Jon Ronander, Tonsberg (NO); Jonathan E. Snyder, Park City, UT (US); Joseph E. Piel, Jr., Scotia, NY (US); Karl Jonsberg, Tonsberg (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 38 days.

(21) Appl. No.: 09/681,318

(22) Filed: Mar. 16, 2001

(65) Prior Publication Data

US 2002/0133078 A1 Sep. 19, 2002

(51) Int. Cl.$^7$ .................................................. A61B 8/00
(52) U.S. Cl. ....................................................... 600/462
(58) Field of Search ................................ 600/437, 443, 600/445, 444, 459, 460, 461, 462; 128/916

(56) References Cited

U.S. PATENT DOCUMENTS

| | | | | |
|---|---|---|---|---|
| 5,050,610 A | * | 9/1991 | Oaks et al. | 600/445 |
| 5,156,155 A | * | 10/1992 | King | 600/44 |
| 5,181,514 A | * | 1/1993 | Solomon et al. | 600/444 |
| 5,402,793 A | * | 4/1995 | Gruner et al. | 600/459 |
| 5,630,417 A | * | 5/1997 | Peterson et al. | 600/445 |
| 5,771,896 A | * | 6/1998 | Sliwa, Jr. et al. | 600/437 |

* cited by examiner

Primary Examiner—Francis J. Jaworski
Assistant Examiner—Maulin Patel
(74) Attorney, Agent, or Firm—McAndrews, Held & Malloy, Ltd.; Peter J. Vogel; Michael A. Dellapenna (57) ABSTRACT

G.E. DOCKET NUMBER 15-DS-00536A system and method for measuring a position of an imaging element located within a scanhead of an imaging probe, such as transesophageal ultrasound probe, is provided. The imaging probe may be used in a medical imaging system and/or a three-dimensional imaging system. The probe includes an articulating portion having a scanhead. The scanhead includes an imaging element, such as a transducer, and a position sensor positioned within the scanhead. Preferably, the position sensor is connected to the imaging element via an axle. Therefore, the rotation of the position sensor is synchronized to the rotation of the imaging element. The location of the position sensor within the imaging element provides accurate measurement of the position of the imaging element. The position sensor preferably includes a code disk having apertures and a system of light emitters and detectors. As the code disk rotates in synchronization with the imaging element, the pattern of detection of light through the apertures measures the position of the imaging element. Various alternative position sensors, such as potentiometers, may be utilized within the scanhead of the probe. The probe also includes a control handle having imaging and articulation controls.

38 Claims, 9 Drawing Sheets

TRANSESOPHAGEAL ULTRASOUND PROBE WITH IMAGING ELEMENT POSITION SENSOR IN SCANHEAD

BACKGROUND OF INVENTION

The preferred embodiment of the present invention generally relates to improvements in an internal imaging probe, and more particularly relates to a transesophageal ultrasound probe with an imaging element position sensor positioned within the scanhead of the probe to detect the position of an imaging element located within the scanhead.

Various medical conditions affect internal organs and structures. Efficient diagnosis and treatment of these conditions typically require a physician to directly observe a patients internal organs and structures. For example, diagnosis of various heart ailments often requires a cardiologist to directly observe affected areas of a patients heart. Instead of more intrusive surgical techniques, ultrasound imaging is often utilized to directly observe images of a patients internal organs and structures.

Transesophageal Echocardiography (TEE) is one approach to observing a patients heart through the use of an ultrasound transducer. TEE typically includes a probe, a processing unit, and a monitor. The probe is connected to the processing unit which in turn is connected to the monitor. In operation, the processing unit sends a triggering signal to the probe. The probe then emits ultrasonic signals into the patients heart. The probe then detects echoes of the previously emitted ultrasonic signals. Then, the probe sends the detected signals to the processing unit which converts the signals into images. The images are then displayed on the monitor. The probe typically includes a semi-flexible endoscope that includes a transducer located near the end of the endoscope. Typically, the transducer is a piezoelectric transducer having 48 to 96 piezoelectric elements.

Typically, during TEE, the endoscope is introduced into the mouth of a patient and positioned in the patients esophagus. The endoscope is then positioned so that the transducer is in a position to facilitate heart imaging. That is, the endoscope is positioned so that the heart or other internal structure to be imaged is in the direction of view of the transducer. Typically, the transducer sends ultrasonic signals through the esophageal wall; the ultrasonic signals come into contact with the heart or other internal structures. The transducer then receives the ultrasonic signals as the ultrasonic signals bounce back from various points within the internal structures of the patient. The transducer then sends the received signals back through the endoscope typically via wiring. After the signals travel through the endoscope, the signals enter the processing unit, typically via wires connecting the endoscope to the processing unit.

Occasionally, the transducer may be rotated about an axis perpendicular to its imaging surface. The transducer may be rotated to change the imaging scan-plane during the imaging process. That is, the transducer may be rotated to image the internal structure from a horizontal scan-plane or a vertical scan-plane (and all positions in between). Typically, the transducer may be rotated 90° in either direction from its normal position.

The position, or orientation, of the transducer is typically measured by a position sensor, such as a potentiometer, located within the control handle of the probe. A mechanical transfer mechanism connects the position sensor located in the control handle to the transducer located in the scanhead. For example, the transducer may be connected to the position sensor via a flexible axle or shaft. Thus, the transducer and the position sensor are typically separated by a significant distance. The separation of the transducer and the position sensor may cause errors in the position measurement. For example, mechanical imperfections, such as slack, spring tension, mechanical hysteresis, or dead zones, may occur due to the extended mechanical distance between the transducer in the scanhead and the position sensor in the control handle. The mechanical imperfections may lead to inaccurate position measurement. The position measurement inaccuracies may lead a physician, or other operator of the probe, to believe that the physician is viewing an internal structure from a scan plane other than the scan plane actually being viewed. For example, the position sensor may measure the position of the transducer at a position 33° from the normal orientation of the transducer when the correct measurement is 30° from the normal orientation. Typically, the position of the transducer measured by the position sensor in the control handle is then displayed on the monitor of the imaging system. Consequently, the physician may misdiagnose and/or mistreat the patient who is being imaged if the deviation is great enough, for example a 10° deviation. Further, smaller errors and deviations, such as a deviation between 3°–5°, typically cause inaccuracies when two-dimensional images are combined to form three-dimensional images.

While the transducer typically images an internal structure in two dimensions, the two-dimensional images may be recorded and combined to produce three-dimensional images. In order to produce three-dimensional images, the transducer is typically rotated through various radial angles thereby imaging various scan-planes. The images from the various scan-planes are recorded and combined using corresponding recorded position measurements. However, inaccuracies in position measurement may skew the resulting three-dimensional images. Further, accurate position measurements are necessary to produce the desired accurate three-dimensional images.

Therefore, a need exists for a more accurate system and method for measuring the position of an imaging element, such as a transducer, within an imaging probe. Specifically, a need exists for an imaging system that provides more accurate measurement of the position of a transducer within a transesophageal ultrasound probe. Additionally, a need exists for an imaging system that provides more accurate measurement of the position of a transducer within an imaging probe to assist in producing accurate three-dimensional images.

SUMMARY OF INVENTION

The present invention relates to an imaging probe, such as a transesophageal ultrasound probe, for use in a medical imaging system and/or a three-dimensional imaging system. The probe includes an articulating portion having a scanhead. The scanhead includes an imaging element, such as a transducer, and a position sensor positioned within the scanhead. Preferably, the imaging element is connected to the position sensor via an axle. Therefore, the imaging element and the position sensor rotate in the same direction and at the same rate as one another. That is, the rotation of the imaging element and the position sensor is synchronized. The location of the position sensor within the scanhead provides accurate measurement of the position of the imaging element.

The position sensor preferably includes a code disk having apertures and a system of light emitters and detectors. As the code disk rotates in synchronization with the imaging element, the pattern of detection of light through the apertures measures the position of the imaging element. Various alternative position sensors, such as potentiometers, may be utilized with the imaging element. The probe also includes a control handle having imaging and articulation controls.

DETAILED DESCRIPTION

Figure 1:
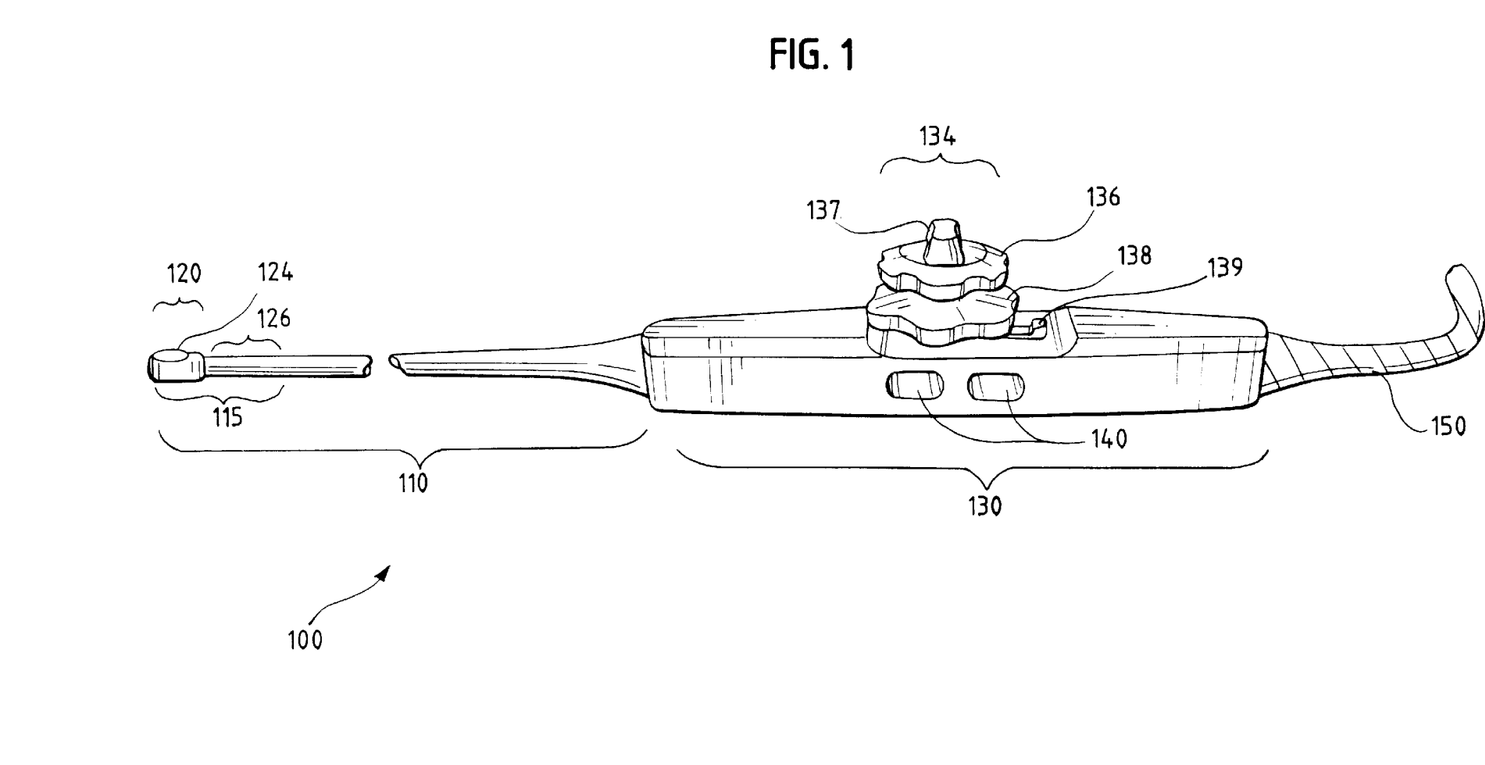
FIG. 1 illustrates a transesophageal ultrasound probe according to a preferred embodiment of the present invention.

FIG. 1 illustrates a transesophageal ultrasound probe 100 according to a preferred embodiment of the present invention. The probe 100 includes a probe shaft 110, a control handle 130, and a system cable 150. The probe shaft 110 includes an articulating portion 115. The articulating portion 115 includes an articulation section 126, and a scanhead 120 having an imaging element window 124. The control handle 130 includes imaging controls 134. The imaging controls 134 include an upper deflection control wheel 136, an upper brake 137, a lower deflection control wheel 138, a lower brake 139 and scan plane push buttons 140.

The probe shaft 110 is fixed to the control handle 130 which is in turn connected to the system cable 150. The articulating portion 115 of the probe shaft ranges from the distal end of the probe shaft 110 to a position approximately 3 inches towards the control handle 130. The articulating portion 115 includes the scanhead 120 connected to the articulation section 126. The scanhead 120 includes an acoustical imaging element window 124. The imaging element window 124 provides an imaging element (not shown), such as a transducer (not shown), imaging access to structures outside of the probe 100.

The probe shaft 110 is connected to the control handle 130. The control handle 130 includes imaging controls 134 that are positioned on the control handle 130. The side of the control handle 130 includes scan-plane push buttons for controlling the positioning of the imaging element. The top of the control handle 130 supports the lower brake 139 and the lower deflection control wheel 138. The lower deflection control wheel 138 is positioned underneath the upper deflection control wheel 136 and the upper brake 137.

The proximal end of the control handle 130 is connected to the system cable 150. The system cable 150 includes wiring (not shown). The wiring extends throughout the system cable 150 into the control handle 130 where it connects to the imaging element within the scanhead 120 of the probe 130 via a signal track (not shown). The system cable 150 is in turn connected to a processing unit (not shown). The imaging element is connected to the processing unit via wiring that extends through the scanhead 120 and throughout the length of the body of the probe 100. The wiring in the probe 100 is then connected via the system cable 150 to the processing unit. The processing unit is then connected via wiring to a monitor (not shown) for displaying images.

Figure 2:
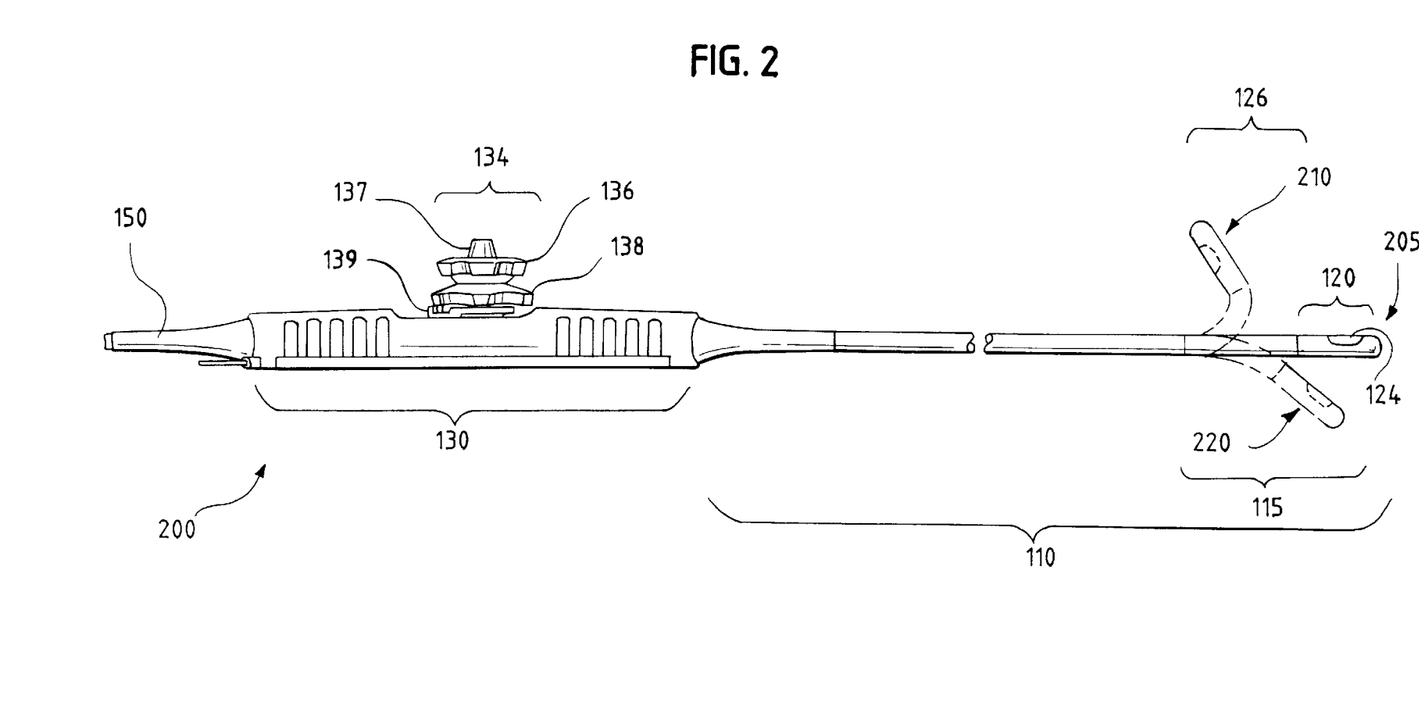
FIG. 2 illustrates a side articulating view of the transesophageal ultrasound probe of FIG. 1 according to a preferred embodiment of the present invention.

FIG. 2 illustrates a side articulating view 200 of the transesophageal ultrasound probe 100 of FIG. 1 according to a preferred embodiment of the present invention. The side articulating view 200 includes the probe shaft 110, the control handle 130, and the system cable 150. The probe shaft 110 includes the articulating portion 115. The articulating portion 115 includes the scanhead 120 having the imaging element window 124 and the articulation section 126. The articulating portion 115 is shown in a non-articulated position 205, an upward articulated portion 210, and a downward articulated portion 220. The control handle 130 includes the imaging controls 134. The imaging controls 134 include the upper deflection control wheel 136, the upper brake 137, the lower deflection control wheel 138, the lower brake 139 and the scan plane push buttons 140 (not shown in FIG. 2).

Figure 3:
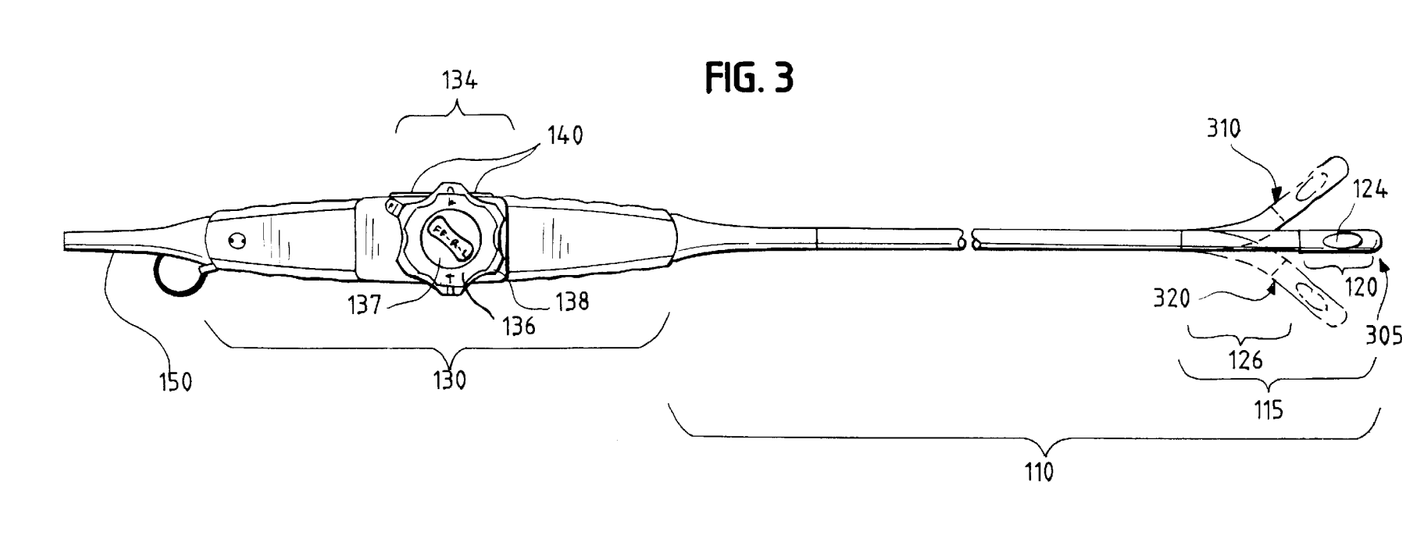
FIG. 3 illustrates a top articulating view of the transesophageal ultrasound probe of FIG. 1 according to a preferred embodiment of the present invention.

FIG. 3 illustrates a top articulating view 300 of the transesophageal ultrasound 100 probe of FIG. 1 according to a preferred embodiment of the present invention. The top articulating view 300 includes the probe shaft 110, the control handle 130, and the system cable 150. The probe shaft 110 includes the articulating portion 115. The articulating portion 115 includes the scanhead 120 having the imaging element window 124 and the articulation section 126. The articulating portion 115 is shown in a non-articulated position 305, a first laterally articulated portion 310, and a second laterally articulated portion 320. The control handle 130 includes the imaging controls 134. The imaging controls 134 include the upper deflection control wheel 136, the upper brake 137, the lower deflection control wheel 138, the lower brake 139 and the scan plane push buttons 140.

In operation, the probe shaft 110 of the probe 100 is introduced into the esophagus of a patient via the patients mouth. The probe shaft 110 is then positioned via the control handle 130 so that an internal structure to be imaged may be imaged by the imaging element through the imaging element window 124. During imaging, the articulating portion 115 of the probe shaft 110 may be articulated in order to provide easier imaging access, or to image internal structures from different angles and perspectives. The articulating portion 115 may be positioned in an upward articulated position 210 or lower articulated position 220 by turning the lower deflection control wheel 138. The articulating portion 115 may be articulated via the lower deflection control wheel 138 ranging from 120° upward to 40° downward and all positions in between. The lower brake 139 may be engaged to lock the articulating portion 115 in an upward or downward articulated position.

Similarly, the articulating portion 115 may be positioned throughout a lateral range. The articulating portion may be positioned in a first laterally articulated portion 310 or a second laterally articulated portion 320 by turning the upper deflection control wheel 136. The articulating portion 115 may be articulated via the upper deflection control wheel 137 ranging from 40° in a first lateral deflection, such as left, to 40° in a second lateral deflection, such as right, and all points in between. The upper brake 137 may be engaged to lock the articulating portion 115 in a laterally articulated position.

Additionally, the articulating portion 115 may be articulated in an upward direction and a lateral direction at the same time. Further, the articulating portion 115 may be articulated in a downward direction and a lateral direction at the same time. Alternatively, the probe 100 may not include lateral articulation capabilities.

During imaging, the imaging element within the scanhead 120 may be rotated about an axis perpendicular to the imaging element window 124. Preferably, the imaging element is a piezoelectric transducer including 48 to 96 piezoelectric elements. As the imaging element is rotated, the scan plane of the imaging element changes. For example, if the imaging element is initially set to image a vertical scan plane, the imaging element may be rotated 90° to image a horizontal scan plane. A position sensor (not shown) positioned within the scanhead 120 and preferably connected to the imaging element, or to another structure that is attached to the imaging element, measures the position, or orientation, of the imaging element. The position sensor then relays the position measurement to the processing unit via wires within the probe 100. The processing unit then displays the position measurement on the monitor. The position measurement displayed on the monitor instructs a physician operating the probe as to the orientation of the image displayed on the monitor. That is, the physician is able to determine the scan plane at which he/she is viewing a patients internal structure. For example, the physician is able to determine whether the physician is viewing a patients internal structure from a horizontal or vertical scan-plane. Additionally, the position measurement may be recorded by the processing unit.

As further described below, in a preferred embodiment of the present invention, the position sensor is located in the scanhead 120 rather than in the control handle 130. The location of the position sensor in the scanhead 120 provides more accurate position measurement. That is, because the position sensor is attached to the imaging element, the imperfections associated with significant distance between the imaging element and the position sensor are alleviated. Therefore, because slack, dead zone, spring tension, mechanical hysteresis and other mechanical phenomena that result in inaccurate position measurement are alleviated, the position measurement is more accurate. Accurate position measurement provides accurate position resolution of the two-dimensional images.

The two-dimensional images may be combined to form accurate three-dimensional images. Forming accurate three-dimensional images via recorded two-dimensional images requires accurate position measurement of the two-dimensional images. Because the position sensor is located in the scanhead 120, the accuracy of the position measurements of the two-dimensional images is increased. The two-dimensional images may be recorded within the processing unit. The processing unit may then combine the recorded two-dimensional images via referencing the position measurements of the two-dimensional images to form three-dimensional images. The resulting three-dimensional images formed from the recorded two-dimensional images are more accurate because the recorded positions of the two-dimensional images are accurate.

After imaging is complete, the articulating portion 115 is returned to the non-articulated positions 205, 305. The probe shaft 110 is then removed from the esophagus of the patient.

Figure 4:
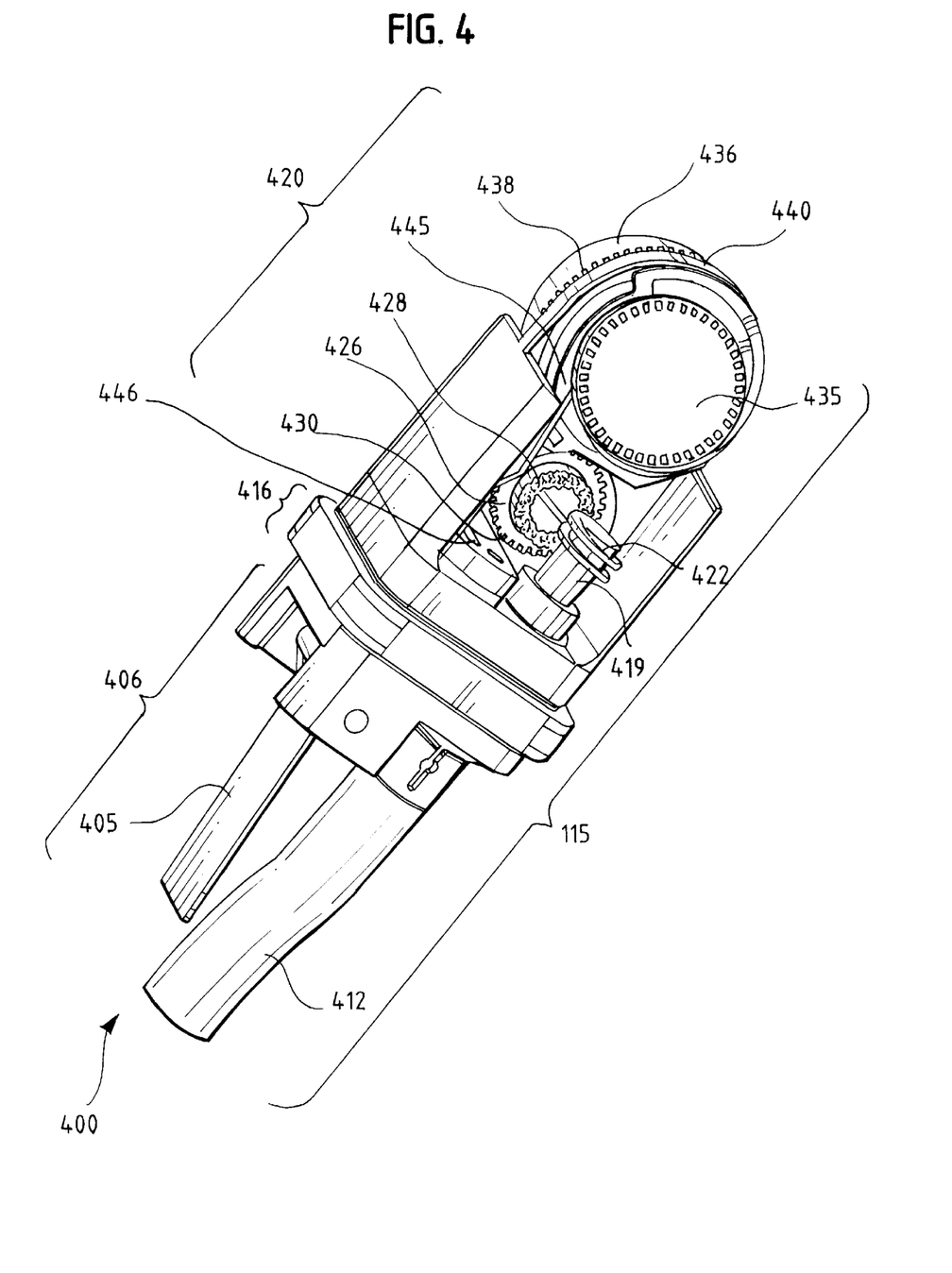
FIG. 4 illustrates an internal view of the scanhead of the transesophageal ultrasound probe of FIG. 1 according to a preferred embodiment of the present invention.

FIG. 4 illustrates an internal view 400 of the scanhead 120 of the transesophageal ultrasound probe 100 of FIG. 1 according to a preferred embodiment of the present invention. The internal view 400 includes the scanhead frame 420, the lower section frame 406, a mechanical support frame 416, a flexible drive shaft 412, a worm screw shaft 419 having a worm screw head 422, and a signal track 445. The scanhead frame 420 includes a distal portion of the worm screw shaft 419 and the worm screw head 422 connected to the worm screw shaft 419. The scanhead frame 420 also includes a rotation wheel 426, an imaging element 436, an imaging element driven cog wheel 438, a bi-directional mounting 440, a track passage 446 and a position sensor disk 435. The rotation wheel 426 includes lateral cogs 428 and longitudinal cogs 430. The lower section frame 406 includes the flexible drive shaft 412 and a proximal portion 405 of the signal track 445.

The scanhead frame 420 is connected to the lower section frame 406 via the mechanical support frame 416. The signal track 445 provides power and signal passage between the imaging element 436 and the processing unit. The proximal portion 405 of the signal track 445 connects to the processing unit via miniature coaxial cables (not shown). The signal track 445 provides electrical connections and signals between the imaging element 436 and the processing unit. The signal track 445 passes through the track passage 446 into the mechanical support frame 416. The signal track 445 passes through the mechanical support frame 416 via an opening (not shown) in the mechanical support frame 416.

The flexible drive shaft 412 extends from the control handle 130 through the probe shaft 110 and into the mechanical support frame 416. The worm screw shaft 419 connects to the flexible drive shaft 412 at the mechanical support frame 416. The worm screw shaft 419 extends into the scanhead frame 420. The mechanical support frame 416 allows passage of the worm screw shaft 419 via an opening (not shown). The worm screw head 422 operatively engages the lateral cogs 428 of the rotation wheel 426. The longitudinal cogs 430 of the rotation wheel 426 operatively engage the imaging element driven cog wheel 438. The imaging element driven cog wheel 438 may be a ring attached to the perimeter of the imaging element 436, or the imaging element driven cog wheel 438 may be included as part of the body of the imaging element 436.

The imaging element 436 is positioned on the bi-directional mounting 440. The bi-directional mounting 440 includes an opening (not shown) formed within the bi-directional mounting 440 that allows for the passage of an axle, as further described below with reference to FIG. 5, that connects the imaging element 440 to the position sensor disk 435.

The position sensor disk 435 may be connected to the imaging element in a variety of ways. Preferably, the imaging element 436 attaches to the position sensor disk 435 via the axle. That is, the axle extends through the imaging element driven cog wheel 438, to connect the imaging element 436 to the position sensor disk 435. Preferably, the position sensor disk 435 is directly fastened to the imaging element 436. Alternatively, the axle may be fastened to the imaging element driven cog wheel 438.

Figure 5:
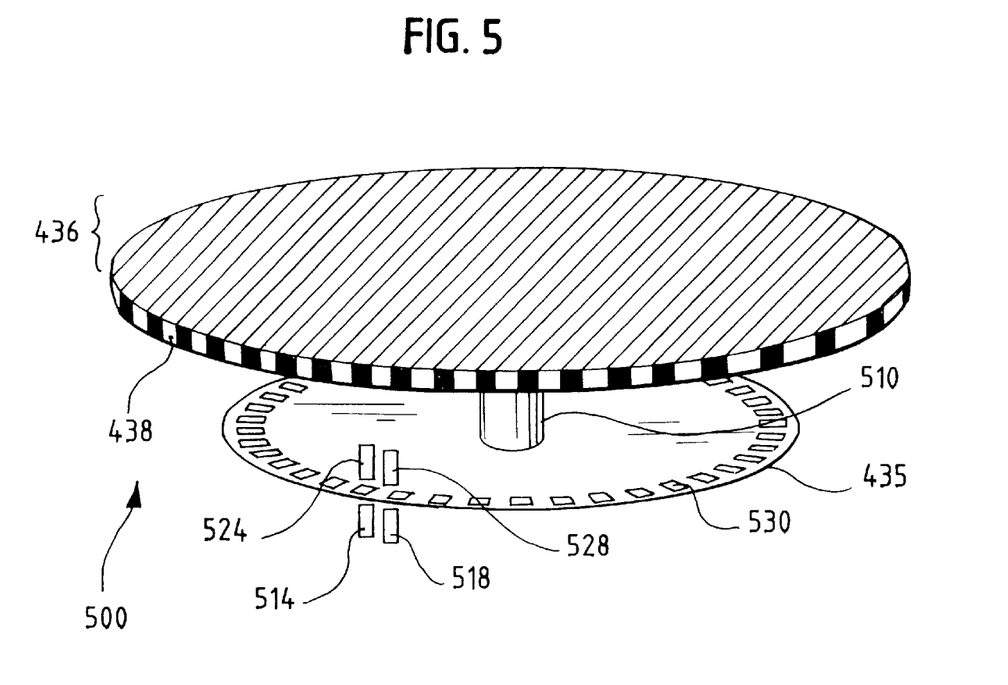
FIG. 5 illustrates a position sensor coupling of the position sensor disk to the imaging element according to a preferred embodiment of the present invention.

FIG. 5 illustrates a position sensor coupling 500 of the position sensor disk 435 to the imaging element 436 according to a preferred embodiment of the present invention. The position sensor coupling includes the imaging element 436, the imaging element driven cog wheel 438, the position sensor disk 435, a first light emitter 524, a second light emitter 528, a first light detector 514, a second light detector 518, a number of apertures 530 radially positioned around the position sensor disk 435, and an axle 510. The axle 510 connects the center of the imaging element 435 to the center of the position sensor 436.

Referring again to FIG. 4, in operation, the scan plane push buttons 140 of FIGS. 1–3 are engaged to rotate the imaging element 436. The scan plane push buttons 140 are connected to a motor (not shown) located in the control handle 130, the probe shaft 110, or at a position within the articulating portion 115. The motor is connected to a proximal portion of the flexible drive shaft 412 which is in turn connected to the worm screw shaft 419. As the motor is engaged, the motor axially rotates the flexible drive shaft 412. The rotation of the flexible drive shaft 412 causes worm screw shaft 419 to rotate. Because the worm screw head 422 is connected to the worm screw shaft 419, the rotation of the worm screw shaft 419 causes the worm screw head 422 to rotate in the same manner.

As the worm screw head 422 rotates, the worm screw head 422 operatively engages the lateral cogs 428 of the rotation wheel 426 causing the rotation wheel 426 to rotate in response to the rotation of the worm screw head 422. Because the lateral cogs 428 and the longitudinal cogs 430 are located on the rotation wheel 426, the rotation of the lateral cogs 428 operatively engages the longitudinal cogs 430 to rotate the longitudinal cogs 430. The rotation of the longitudinal cogs 430 operatively engages the imaging element driven cog wheel 438 to rotate the imaging element driven cog wheel 438 in the opposite direction as that of the rotation wheel 426. The rotation of the imaging element driven cog wheel 438 in turn causes the imaging element 436 to rotate in the same direction as that of the imaging element driven cog wheel 438. Because the position sensor disk 435 is axially connected to the imaging element 436 via the axle 510, the position sensor disk 435 axially rotates at the same rate, and in the same direction, as the imaging element 436. That is, the rotation of the imaging element 436 is synchronized to the rotation of the position sensor disk 435. As further described below, the position sensor including the position sensor disk 435 accurately measures the position of the imaging element 436. The position sensor including the position sensor disk 435 relays the position of the imaging element to the processing unit via wiring or through the signal track 445.

Alternatively, various types of engaging members may be used to rotate the imaging element 436. For example, a semi-flexible rotating axle may be used in place of the flexible drive shaft 412. Additionally, a series of push/pull wires may be used to control the rotation of the imaging element 436.

Figure 6:
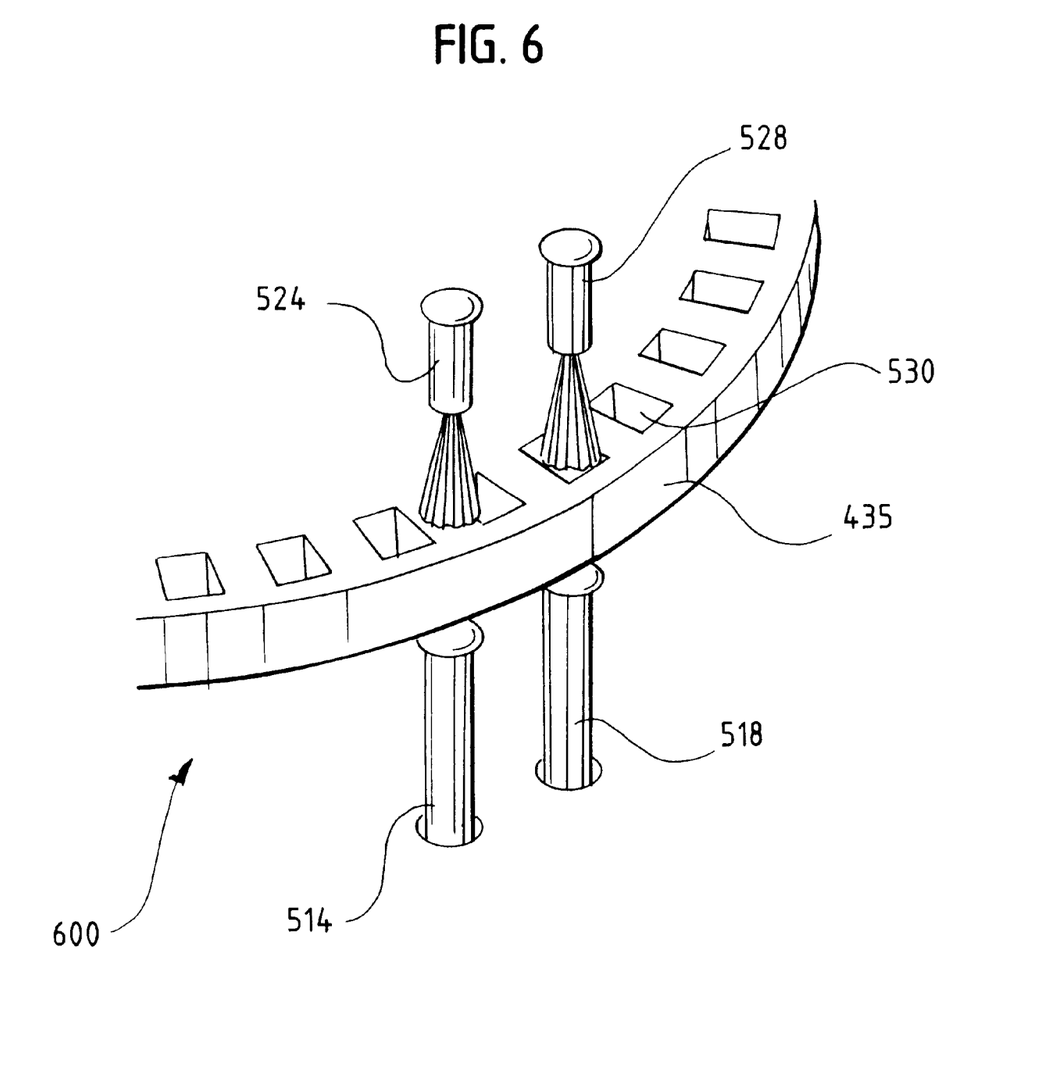
FIG. 6 illustrates a close view of the position sensor of FIG. 4 according to a preferred embodiment of the present invention.

FIG. 6 illustrates a close view 600 of the position sensor according to a preferred embodiment of the present invention. Preferably the position sensor is an optical sensor that includes the position sensor disk 435, the first light detector 514, the second light detector 518, the first light emitter 524 and the second light emitter 528. Preferably, the position sensor disk 435 is a code disk. The position sensor disk 435 includes the apertures 530 radially positioned around the position sensor disk 435. The first and second light emitters 524, 528 and the first and second light detectors 514, 518 preferably are formed into a single integrated structure (not shown). The structure is preferably attached to the interior of the probe 100. Preferably, the structure is shaped to allow the position sensor disk 435 to pass between the first and second light emitters 524, 528 and the first and second light detectors 514, 518 as shown.

The first light detector 514 is aligned with the first light emitter 524. The first light emitter 524 continuously emits light that is detected by the first light detector 514. The second light detector 518 is aligned with the second light emitter 528. The second light emitter 528 continuously emits light that is detected by the second light detector 518. The position sensor disk 435 is opaque and thus blocks light. For example, when an aperture 530 of the position sensor disk 435 is positioned between the first light detector 514 and the first light emitter 524, light passes through the aperture 530 and the first light detector 514 detects light. However, if the position sensor disk 435 is rotated so that no aperture 530 is positioned between the first light emitter 524 and the first light detector 514, the position sensor disk 435 blocks the light emitted by the first light emitter 524 and thus the first light detector 524 does not detect light.

The apertures 530 are offset relative to the first and second light emitters 524, 528 and the first and second light detectors 514, 518. That is, when the first light detector 514 detects light, the second light detector 518 detects only a portion of light emitted from the second light emitter 528, or does not detect light at all. Also, when the second light detector 518 detects light, the first light detector 514 detects only a portion of light emitted from the first light emitter 524, or does not detect light at all. Thus, as further describe below with respect to FIG. 8, as the position sensor disk 435 rotates, the signals of the first and second light detectors 514, 518 may be compared to determine the direction and speed of the rotation of the position sensor disk 435.

The direction of the rotation of the position sensor disk 435, such as a code disk, may be determined by the sequence of the signals from the first and second light detectors 514, 518. The speed of the position sensor disk 435 may be determined by the frequency of transitions detected by the first and second light detectors 514, 518. Therefore, as the position sensor disk 435 rotates, the magnitude and direction of the movement of the position sensor 435 may be measured through the light signals received by the first and second light detectors 514, 518. Because the position sensor disk 435 rotates at the same rate and in the same direction as the imaging element 436, the rotation of the position sensor disk 435 matches, that is, is synchronized to, the rotation of the imaging element 436. Therefore, the rotation of the imaging element 436 may be determined from the rotation of the position sensor disk 435.

Figure 8:
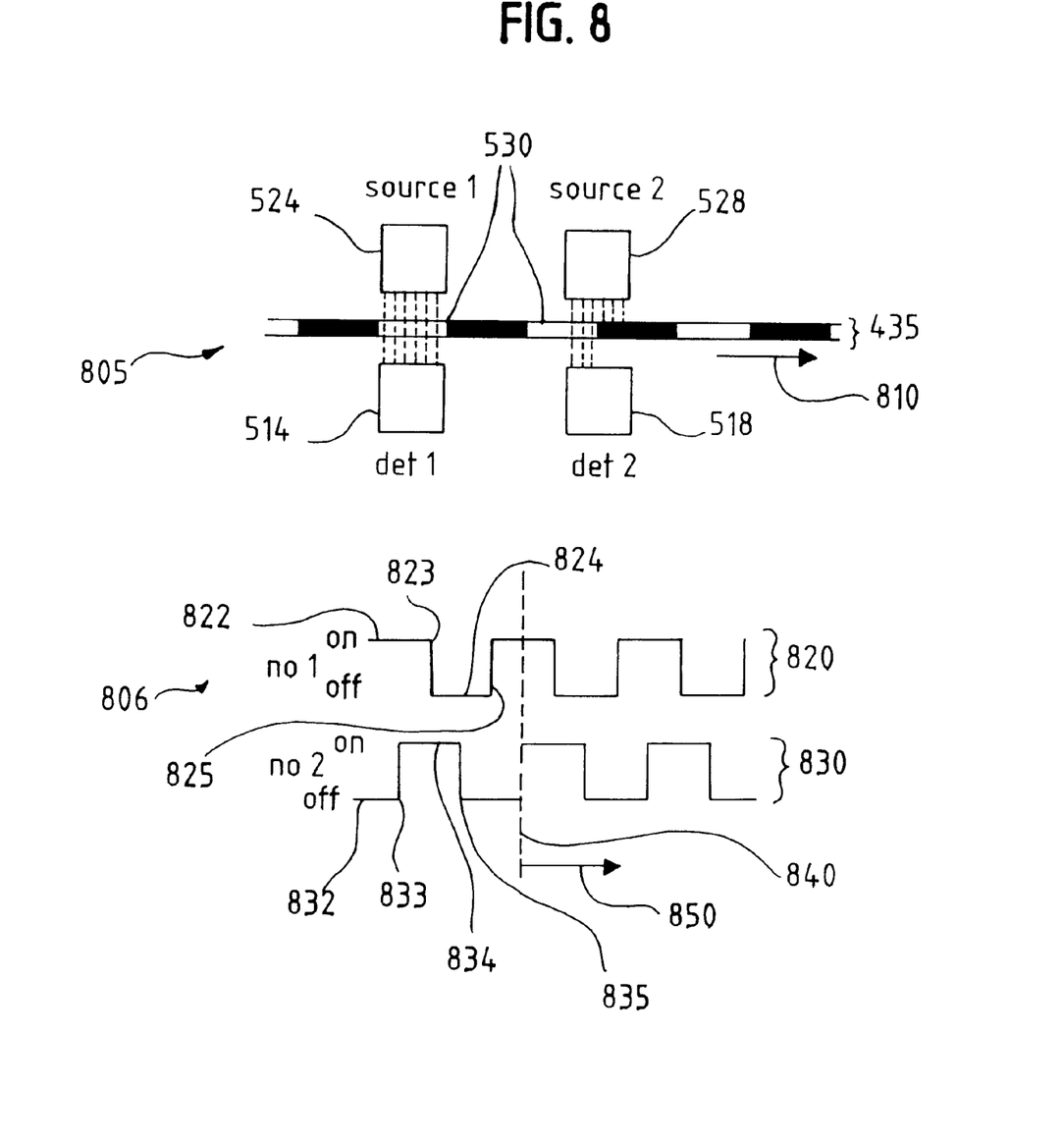
FIG. 8 illustrates a timing diagram of the position sensing process according to a preferred embodiment of the present invention.

FIG. 8 illustrates a timing diagram 800 of the position sensing process according to a preferred embodiment of the present invention. The timing diagram 800 includes a rotation diagram 805 and a transition pulse diagram 806. The rotation diagram 805 includes the position sensor disk 435, such as a code disk, the first light emitter 524, the first light detector 514, the second light emitter 528, the second light detector 518, the apertures 530, and an arrow 810 defining the direction of rotation of the position sensor disk 435. The transition pulse diagram 806 includes a first transition pulse sequence 820 corresponding to the first light detector 514, a second transition pulse sequence 830 corresponding to the second light detector 518, a reference time-line 840, and an arrow 850 corresponding to advancing time.

The first transition pulse sequence 820 includes logical high pulses, for example logical high pulse 822, high-to-low transitions, for example high-to-low transition 823, low-tohigh transitions, for example low-to-high transition 825, and logical low pulses, for example logical low pulse 824. The second transition pulse sequence 830 includes logical low pulses, for example logical low pulse 832, low-to-high transitions, for example low-to-high transition 833, high-to-low transitions, for example high-to-low transition 835, and logical high pulses, for example logical high pulse 834. The specific instant in time shown in the rotation diagram 805 is represented in the transition pulse diagram 806 by the reference time-line 840.

The first light detector 514 emits a logical high pulse when the first light detector 514 detects light. The first light detector 514 emits a logical low pulse when the first light detector 514 does not detect light. Transitions occur at a logical cut-off, such as 50% of the maximum amplitude of the light emitted by the first light detector 514. For example, a low-to-high transition occurs when the first light detector 514 emits a logical low pulse and then detects 50% or more of the maximum amplitude of the light emitted by the first light emitter 524. A high-to-low transition occurs when the first light detector 514 emits a logical high pulse and then detects less than 50% of the maximum amplitude of the light emitted by the first light emitter 524.

Similarly, the second light detector 518 emits a logical high pulse when the second light detector 518 detects light. The second light detector 518 emits a logical low pulse when the first second detector 518 does not detect light. Transitions occur at a logical cut-off, such as 50% of the maximum amplitude of the light emitted by the second light detector 518. For example, a low-to-high transition occurs when the second light detector 518 emits a logical high pulse and then detects 50% or more of the maximum amplitude of the light emitted by the second light emitter 528. A high-to-low transition occurs when the first light detector emits a logical high pulse and then detects less than 50% of the maximum amplitude of the light emitted by the second light emitter 528.

The direction of movement of the position sensor disk 435 determines the sequence of transitions of the first and second light detectors 514, 518. As the position sensor disk 435 moves in the direction denoted by the arrow 810, a low-to-high transition pulse of the second transition pulse sequence 830 precedes a high-to-low transition of the first transition pulse sequence 820. The sequence of transitions is registered by the position sensor in order to determine the direction of rotation of the position sensor disk 435. Conversely, as the position sensor 435 rotates in a direction opposite that of the arrow 810, a low-to-high transition of the first transition pulse sequence 820 precedes a high-to-low transition pulse of the second transition pulse sequence 830. Therefore, as the sequence of transitions is registered, the direction of rotation of the position sensor disk 435 may be determined.

Alternatively, the optical system may be reflective rather than aperture based. That is, the position sensor disk 435 may include reflectors, instead of apertures 530, radially positioned around the position sensor disk 435 and separated by non-reflective surfaces. If the position sensor disk 435 includes reflectors, the first and second light emitters 524, 528 and the first and second light detectors 514, 518 may be located on the same side of the position sensor disk 435. The first and second light emitters 524, 528 and first and second light detectors 514, 518 may be angled such that the first and second light emitters 524, 528 emit light that reflects from the reflectors on the position sensor disk 435. However, no light is reflected when the first and second light emitters 524, 528 emit light that contacts a non-reflective surface. For example, the first and second light emitters 524, 528 may be positioned to emit light that strikes the passing reflectors at a 45° angle of incidence. Therefore, the first and second light detectors 514, 518, may be positioned to detect the light reflected at a corresponding 45° angle of reflection.

Figure 9:
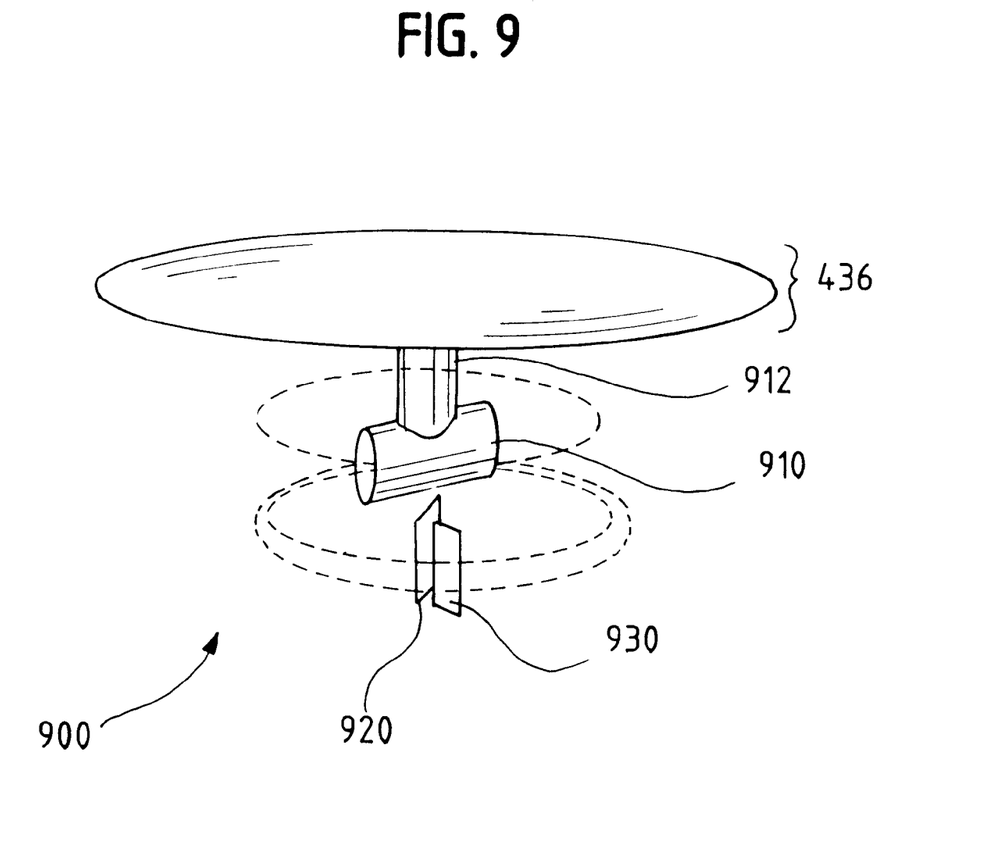
FIG. 9 illustrates a magnetic sensor coupling of a magnetic position sensor to the imaging element according to an alternative embodiment of the present invention.

FIG. 9 illustrates a magnetic sensor coupling 900 of a magnetic position sensor to the imaging element 436 according to an alternative embodiment of the present invention. The magnetic sensor coupling 900 includes the imaging element 436, an axle 912, a magnet 910, a first magnetic field detector 920 and a second magnetic field detector 930. The imaging element 436 is connected to the magnet 910 via the axle 912. Preferably, the first magnetic field detector 920 and the second magnetic field detector 930 are Hall detectors. Additionally, preferably the first magnetic field detector 920 and the second magnetic field detector 930 are angled 90° relative to one another and are positioned underneath the magnet 910. The first magnetic field detector 920 and the second magnetic field detector 930 are attached to the interior of the scanhead 120. The magnetic field of the magnet 910 is a non-uniform magnetic field. That is, one side of the magnet has a different magnetic polarity than the other side of the magnet.

In operation, the magnetic field detectors 920, 930 sense the magnetic field from the magnet 910. The output from the magnetic field detectors 920, 930 is proportional to the magnetic flux on the surface of the magnetic field detectors 920, 930. Therefore, the output from the first magnetic field detector 920 is minimal when the magnetic field is parallel to the surface of the first magnetic field detector 920; and the output from the second magnetic field detector 930 is minimal when the magnetic field is parallel to the surface of the second magnetic field detector 930. Thus, as the imaging element 436 rotates, the magnets magnetic field that is perceived by the magnetic field detectors 920, 930, and the output from the magnetic field detectors 920, 930 change. When the output from the first magnetic field detector 920 is at a maximum value, the output from the second magnetic field detector 930 is at a minimum value, and vice versa. Alternatively, one magnetic field detector may be used instead of two magnetic field detectors. Two magnetic field detectors, however, provide better resolution and accuracy.

Also, alternatively, the position sensor may be a potentiometer. Typically, a potentiometer is calibrated to a normal position. When the position of the potentiometer is changed, the potentiometer translates the change in position through an electrical resistance value. Consequently, the rotation of the imaging element causes the resistance value of the potentiometer to change. The resistance value is then relayed to the processing unit.

Additionally, the position sensor may be an inductive position sensor. The inductive position sensor may include a fixed coil and a coil attached to the imaging element 436. For example, the fixed coil may be fixed to an interior portion of the scanhead 120. As the imaging element coil moves, the inductance between the coils changes. Deviations from a preset calibrated inductance may then be used by a detector to measure the position of the imaging element.

Further, the position sensor may be a capacitive position sensor. The position sensor disk 435 may include one or more conductive plates fixed within the scanhead 120 and a number of conductive plates radially positioned to the position sensor disk 435. As the position sensor disk 435 rotates, the plates of the position sensor disk 435 rotate. The capacitance between the fixed plates and the plates on the position sensor disk 435 changes. Deviations from a preset calibrated capacitance may then be detected by a voltage detector and used to measure the position of the imaging element.

Figure 7:
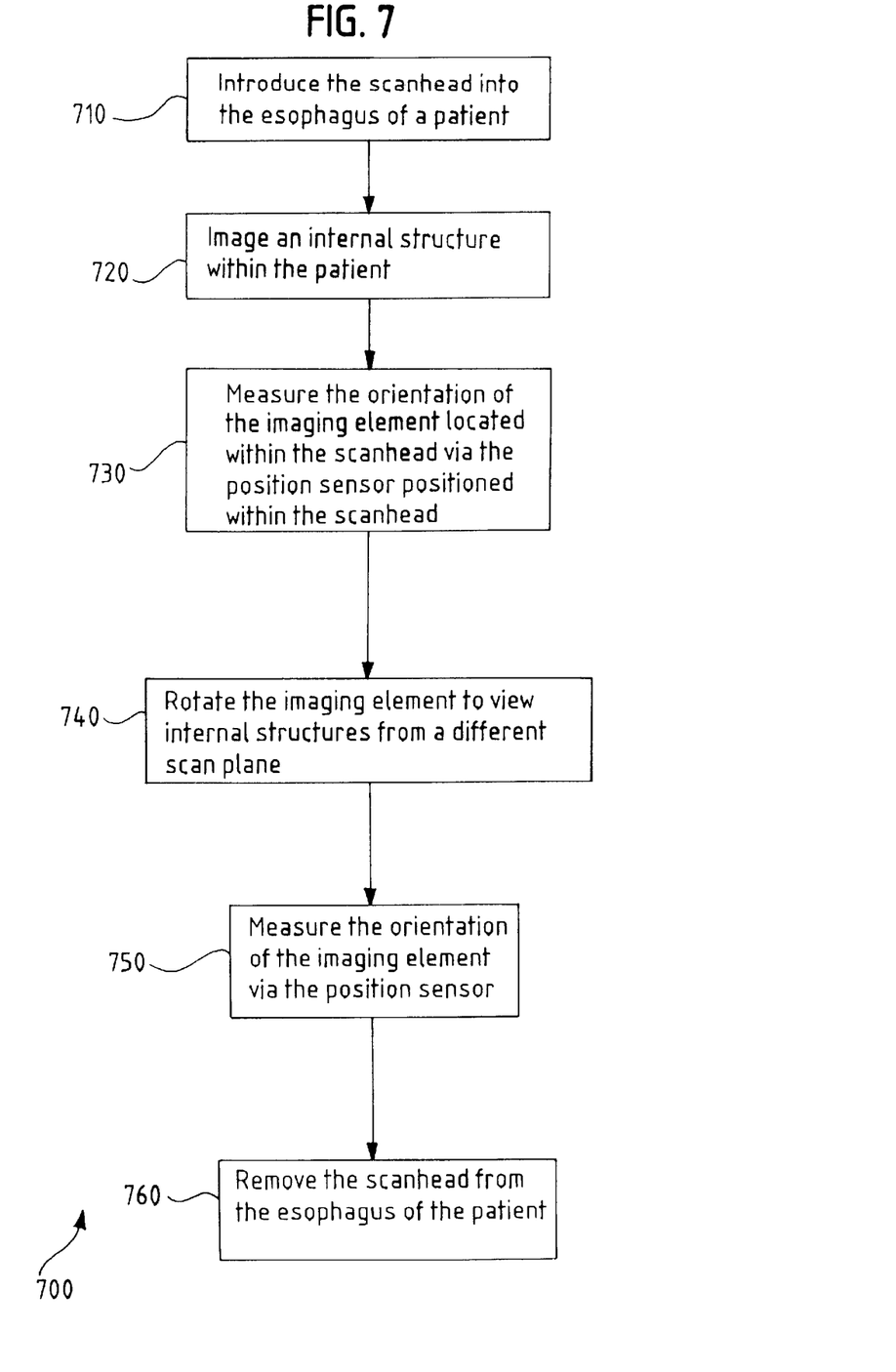
FIG. 7 illustrates a flow chart according to a preferred embodiment of the present invention.

FIG. 7 illustrates a flow chart 700 of the imaging process according to a preferred embodiment of the present invention. At step 710, a physician begins the imaging process by introducing the scanhead 120 located on the articulating portion 115 of the probe shaft 110 into the esophagus of a patient. The articulating portion 115 of the probe 100 may be articulated during imaging. At step 720, the physician engages the probe 100 to image an internal structure of a patient.

The orientation of the imaging element 436 is measured with the position sensor 435 in the scanhead 120 of the probe 100 at step 730. Preferably, the position sensor 435 is connected onto the axle 510 which in turn connects to the imaging element 436 or the imaging element driven cog wheel 438. The imaging element driven cog wheel 438, the axle 510 and the position sensor 435 are located within the scanhead 120 as further described above.

At step 740, the physician may rotate the imaging element 436 to view the internal structure from a different scan plane. At step 750, the orientation of the imaging element 436 is again measured via the position sensor 435. After imaging is complete, the physician removes the scanhead 120 of the probe shaft 110, and the probe shaft 110 from the esophagus of the patient at step 760.

Thus, the present invention provides an improved system and method for measuring the position of an imaging element, such as a transducer, within an imaging probe. Particularly, the present invention provides an improved system and method for accurately measuring the position of a piezoelectric transducer within a transesophageal ultrasound probe. Accurate measurement of the position of the imaging element is achieved via locating a position sensor within the scanhead of the probe where the measurement of the imaging element may be determined without the mechanical imperfections associated with prior art probes.

Locating the position sensor 435 within the scanhead 120 of the imaging element 436 provides more accurate measurement of the position and orientation of the imaging element 436. Accurate measurement of the position of the imaging element 436 facilitates more accurate diagnosis and treatment. Additionally, the resultant images may be combined via referencing position measurements to form accurate three-dimensional images and/or illustrations. The accurate measurement of the position of the imaging element 436 enables three-dimensional imaging because accurate position measurements are required to combine the recorded images into a single image.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features which come within the spirit and scope of the invention.

What is claimed is:

1. A system for determining the position of an imaging element located within a scanhead of an internal imaging probe, said system including a position sensor located in said scanhead of said probe, wherein said position sensor is an optical sensor, and wherein said optical sensor includes a plurality of light emitters and a plurality of light detectors.

2. The system of claim 1 wherein said imaging element includes a scan plane, said imaging element rotating to vary said scan plane.

3. The system of claim 1 further including a position sensor disk, said position sensor disk having apertures radially positioned around said position sensor disk.

4. The system of claim 1 further including a position sensor disk, said position sensor disk having reflectors radially positioned around said position sensor disk.

5. The system of claim 1 wherein said optical sensor includes:
   a position sensor disk having at least one of apertures and reflectors radially positioned around said position sensor disk, said position sensor disk being positioned between said light emitters and said light detectors.

6. The system of claim 1 further including a control handle including imaging controls, said imaging controls controlling said position of said imaging element.

7. A system for determining the position of an imaging element located within a scanhead of an internal imaging probe, said system including a position sensor located in said scanhead of said probe wherein said position sensor includes at least one of an inductive position sensor, a capacitive position sensor, and a magnetic position sensor.

8. An imaging probe for use in a medical imaging system, said probe including an articulating portion having a scanhead, said scanhead including:
   an imaging element; and
   a position sensor mechanically connected to said imaging element, said position sensor measuring a position of said imaging element, wherein said position sensor is an optical sensor, and wherein said optical sensor includes a plurality of light emitters and a plurality of light detectors.

9. The probe of claim 8 wherein said imaging element includes a scan plane, said imaging element rotating to vary said scan plane.

10. The probe of claim 8 further including a code disk, said code disk having apertures radially positioned around said code disk.

11. The probe of claim 8 further including a code disk, said code disk having reflectors radially positioned around said code disk.

12. The probe of claim 8 wherein said position sensor includes:
   a position sensor disk having at least one of apertures and reflectors radially positioned around said code disk, said code disk being positioned between said light emitters and said light detectors.

13. The probe of claim 8 further including a control handle including imaging controls, said imaging controls controlling said position of said imaging element.

14. An imaging probe for use in a medical imaging system, said probe including an articulating portion having a scanhead, said scanhead including:
   an imaging element; and
   a position sensor mechanically connected to said imaging element, said position sensor measuring a position of said imaging element wherein said position sensor includes at least one of an inductive position sensor, a capacitive position sensor, and a magnetic position sensor.

15. A method of measuring the position of an imaging element located in a scanhead of an internal imaging probe including the step of measuring the position of said imaging element via a position sensor within said scanhead wherein said measuring step includes measuring with an optical sensor within said scanhead.

16. The method of claim 15 wherein said measuring step includes measuring the position of said imaging element while said imaging element rotates to image an internal structure of a patient from a different scan plane.

17. The method of claim 15 further including the step of introducing said scanhead into the esophagus of said patient.

18. The method of claim 15 further including the step of rotating said transducer during said imaging.

19. The method of claim 15 wherein said measuring step includes measuring via a plurality of light emitters and light detectors within said scanhead.

20. The method of claim 19 wherein said measuring step includes rotating an optical disk having apertures between said light emitters and said light detectors.

21. The method of claim 19 wherein said positioning step includes rotating an optical disk having reflectors between said light emitters and said light detectors.

22. A method of measuring the position of an imaging element located in a scanhead of an internal imaging probe including the step of measuring the position of said imaging element via a position sensor within said scanhead, wherein said measuring step includes measuring via a potentiometer within said scanhead.

23. A method of measuring the position of an imaging element located in a scanhead of an internal imaging probe including the step of measuring the position of said imaging element via a position sensor within said scanhead wherein said measuring step includes measuring with at least one of an inductive position sensor and a capacitive position sensor within said scanhead.

24. A three-dimensional imaging system including an internal imaging probe having a scanhead, said scanhead including:
   an imaging element; and
   a position sensor, said position sensor measuring an orientation of said imaging element.

25. The system of claim 24 wherein said imaging element includes a scan plane, said imaging element rotating to vary said scan plane.

26. The system of claim 24 wherein said position sensor is an optical sensor.

27. The system of claim 26 wherein said optical sensor includes a plurality of light emitters and light detectors.

28. The system of claim 26 further including a position sensor disk, said position sensor disk having apertures radially positioned around said position sensor disk.

29. The system of claim 26 further including a position sensor disk, said position sensor disk having reflectors radially positioned around said position sensor disk.

30. The system of claim 24 wherein said position sensor includes:
   a plurality of light emitters and light detectors; and
   a position sensor disk having at least one of apertures and reflectors radially positioned around said code disk, said code disk being positioned between said light emitters and said light detectors.

31. The system of claim 24 wherein said position sensor is a potentiometer.

32. The system of claim 24 wherein said position sensor includes at least one of an inductive position sensor, a capacitive position sensor, and a magnetic position sensor.

33. The system of claim 24 wherein said probe includes a control handle including imaging controls, said imaging controls controlling said position of said imaging element.

34. The system of claim 24 further including a processing unit, said processing unit recording two-dimensional images imaged by said imaging element.

35. The system of claim 24 further including a processing unit, said processing unit combining two-dimensional images imaged by said imaging to form three-dimensional images.

36. A system for determining the position of an imaging element located within a scanhead of an internal imaging probe, said system including a position sensor located in said scanhead of said probe wherein said position sensor includes at least one of an inductive position sensor and a capacitive position sensor.

37. An imaging probe for use in a medical imaging system, said probe including an articulating portion having a scanhead, said scanhead including:
   an imaging element; and
   a position sensor mechanically connected to said imaging element, said position sensor measuring a position of said imaging element wherein said position sensor includes at least one of an inductive position sensor and a capacitive position sensor.

38. A three-dimensional imaging system including an internal imaging probe having a scanhead, said scanhead including:
   an imaging element; and
   a position sensor, said position sensor measuring an orientation of said imaging element, wherein said position sensor includes at least one of an inductive position sensor and a capacitive position sensor.

* * * * *